United States Patent [19]

Glaros

[11] Patent Number: 5,376,088
[45] Date of Patent: Dec. 27, 1994

[54] ELECTRONIC HAIR REMOVER

[76] Inventor: Nicholas G. Glaros, 21666 Little Bear La., Boca Raton, Fla. 33428

[21] Appl. No.: 986,669

[22] Filed: Dec. 8, 1992

Related U.S. Application Data

[62] Division of Ser. No. 586,495, Sep. 21, 1990, Pat. No. 5,169,398.

[51] Int. Cl.⁵ .............................................. A61B 17/41
[52] U.S. Cl. .................................... 606/36; 606/43; 606/51; 606/52
[58] Field of Search ..................... 606/36, 42, 43, 51, 606/52

[56] References Cited

U.S. PATENT DOCUMENTS

| | | |
|---|---|---|
| 853,096 | 5/1907 | Lewis . |
| 1,071,978 | 9/1913 | White . |
| 2,249,894 | 7/1941 | Goldenstein . |
| 2,417,530 | 3/1947 | Weiser . |
| 2,477,467 | 5/1949 | Rose . |
| 2,700,975 | 2/1955 | Hopfinger et al. . |
| 2,888,927 | 6/1959 | Foxard . |
| 2,894,512 | 7/1959 | Tapper . |
| 3,054,405 | 9/1962 | Tapper . |
| 3,315,678 | 4/1967 | Donelson . |
| 3,359,982 | 12/1967 | Guiorguiev . |
| 3,831,607 | 8/1974 | Lindemann . |
| 3,916,909 | 11/1975 | Kletschka et al. . |
| 4,033,350 | 7/1977 | Hoshi . |
| 4,041,952 | 8/1977 | Morrison, Jr. et al. . |
| 4,167,187 | 9/1979 | Biagi . |
| 4,174,714 | 11/1979 | Mehl . |
| 4,321,926 | 3/1982 | Roge . |
| 4,878,493 | 11/1989 | Pasternak et al. ................... 606/42 |
| 4,994,061 | 2/1991 | McPherson ........................ 606/43 |

*Primary Examiner*—Lee S. Cohen
*Attorney, Agent, or Firm*—McAndrews, Held & Malloy, Ltd.

[57] ABSTRACT

An electronic hair remover which uses high radio frequency energy to aid in the removal or treatment of hair. The remover includes a single hand-held casing containing an RF generator in electrical connection to a power source. A pulse timer unit and an interface unit cooperated with the RF generator to generate a treatment signal. The RF energy developed by the RF generator is emitted from the remover in pulses of high amplitude voltage of short duration with the amplitude being automatically adjusted in response to a characteristic of skin proximity. A tweezer assembly extends from the casing and has two opposing electrically conductive tweezer tips across which the electrical energy is supplied.

14 Claims, 3 Drawing Sheets

ELECTRONIC HAIR REMOVER

This is a divisional of application Ser. No. 07/586,495 filed Sep. 21, 1990, now U.S. Pat. No. 5,169,398.

BACKGROUND OF THE INVENTION

The present invention relates to an electronic hair remover which permits a user to remove unwanted hair, a single hair at a time.

Heretofore, unwanted hair has been removed by a high frequency coagulation of the hair root. The hair is initially gripped by a pair of tweezers, or located within the proximity of an electrified needle, and a high frequency electrical wave is applied to the hair.

One of the earliest instruments for removing hair with electric current is disclosed in U.S. Pat. No. 853,096 (Lewis 1907). Lewis' depilatory instrument includes a handle, a forceps, a needle, and means for supplying an electric current to the needle. Similarly, U.S. Pat. No. 1,071,978 (White 1913) discloses a device for removing hairs with tweezer blades which are connected to the terminals of an electric circuit. U.S. Pat. No. 2,417,530 (Weiser 1947) discloses an electrical hair removing instrument with which the hair is first pulled by a tweezer and the resulting hole treated with electrical current. Except for the use of a low current, no particular safety features were used in these early devices.

In an attempt to deal with the safety of hair removal, U.S. Pat. No. 2,888,927 (Fozard 1959) discloses an apparatus for removal of superfluous hair in which the gripping means are adapted to grip a hair at a point spaced from the skin. Thus, when high frequency current energizes the gripping means, the high frequency current passes along the hair to coagulate or otherwise destroy the hair bulb. This permits the apparatus to be used by the non-professional consumer. However, Fozard does not disclose an apparatus which avoid burns in the event that the tweezers inadvertently contact the skin.

U.S. Pat. No. 2,894,512 (Tapper 1959) discloses an epilation device for one-handed operation in which forceps are used to engage a single hair. Tapper's device can be used by a non-professional consumer and held in only one hand, but no safety mechanisms other than a rheostat are disclosed.

Subsequently, devices began using approaches to provide safety from skin burns. U.S. Pat. No. 4,174,714 (Mehl 1979) and U.S. Pat. No. 4,033,350 (Hoshi 1977) disclose such devices which use high frequency electrical waves. Mehl uses an insulating layer on the tweezers, in an assembly held by an operator, which in turn is attached by a cable to an energy source. As an additional feature, Mehl uses only an upper tweezer arm to conduct the high frequency electrical waves. Hoshi uses either a heat insulating cover on the hair clamping members or a safety guide adapted to keep the tips of the hair clamping members out of direct contact with the skin. However, such structures prove to be cumbersome and result in bulky devices which are unwieldy for the users.

An approach to the problem of alleviating pain during an epilation treatment is disclosed in U.S. Pat. No. 2,700,975 (Hopfinger et. al. 1955). Hopfinger discloses an apparatus which can produce at least two high frequency currents of predetermined and different intensities. A time controlled switching mechanism allows the operator to switch from a relatively low intensity, short duration pulse, to a longer duration, higher intensity pulse by mechanical means such as foot pedals and switches.

As a result, the operator using Hopfinger's device can initiate a series of shorter, low intensity pulses, and thereafter the occurrence of pulses of longer duration and greater intensity. Hopfinger relies on this plurality of low intensity pulses to produce a coagulated layer around the papilla, thus impeding the high intensity pulse from reaching the nerve nearest the hair. However, Hopfinger discloses no safety mechanism if the needle contacts the skin.

Consequently, despite the prior art, a need still exists for a hair removal device which is both simple and easily manipulated by the user while at the same time protects the user from electrical burns.

It is therefore an object of the present invention to provide an electronic hair remover having tweezer-like metal ends which are similar to a conventional pair of tweezers. This permits the non-professional user to manipulate apparatus with which the user is familiar.

It is a further object of the invention to provide an electronic hair remover which will not cause skin burns from inadvertent contact of the tweezers with the skin.

It is a further object of the invention to provide an electronic hair remover which provides pulsed high energy bursts to tweezer tips to treat the root of a hair.

It is a further object of the invention to provide an electronic hair remover in which the presence of a hair is detected prior to application of electric current to the tweezer tips.

It is a further object of the invention to provide an electronic hair remover in which the occurrence of skin contact is detected prior to application of electric current to the tweezer tips.

It is a further object of the present invention to provide an electronic hair remover which comprises a self-contained hand held unit which is pleasing in appearance and convenient to use by a non-professional user.

It is a further object of the present invention to provide an electronic hair remover which can be battery powered.

SUMMARY OF THE INVENTION

These and other objects of the invention are achieved in an electronic hair remover using high radio frequency (RF) energy to remove the hair. The hair remover comprises a single hand-held unit with a projecting tweezer-like structure having conventional metal tweezer tips. An RF generator provides energy across the tweezer structure in accordance with the physical distance between the tweezer tips and the skin. In one embodiment, short duration energy bursts are output from the hair remover, and continuous monitoring of possible skin contact provides a safe, easy to use, tweezer unit.

DETAILED DESCRIPTION OF THE PREFERRED EMBODIMENT

Figure 1:
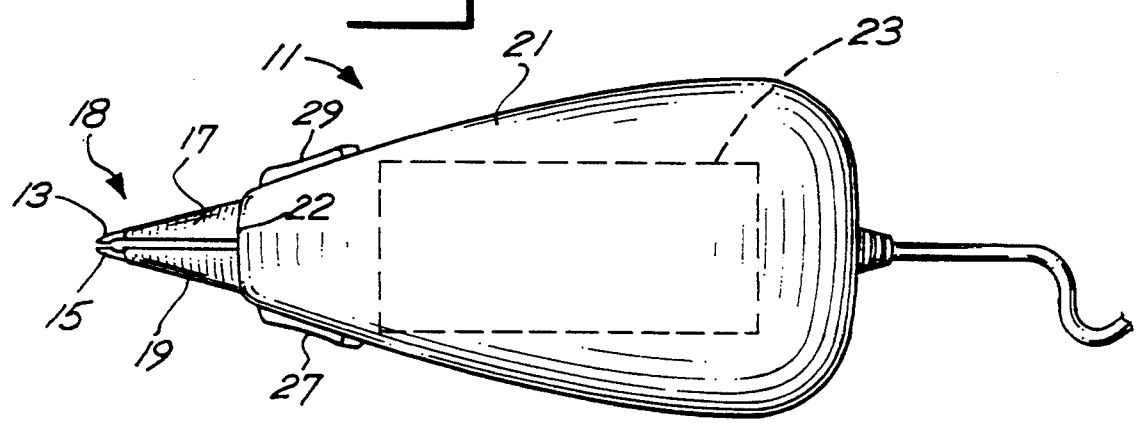
FIG. 1 is a top view of one embodiment of an electronic hair remover of the present invention.

Referring to FIG. 1, an electronic hair remover 11 includes a generally pear-shaped casing 21 which is shaped to permit its holding solely by one hand of the user. Casing 21 is connected to a tweezer assembly 18 formed of a pair of tweezer arms 17, 19 which carry respective tweezer tips 13, 15.

Tweezer tips 13, 15 are made of an electrically conducting material, preferably metal, and are sized and shaped like conventional tips of a conventional pair of tweezers. Tweezer tips 13, 15 serve to grip a single hair for application of a high amplitude, radio frequency (RF), electrical signal to the hair. The signal travels down the hair shaft to treat the hair root. After which, the hair may be removed from the skin by using the tweezer tips to grip and pull the hair out of the skin.

Tweezer arms 17, 19 may be covered with plastic for insulation purposes and allows the assembly to be a low cost molded structure. The arms project outwardly from the distal end 22 of casing 21 in a generally parallel relationship to each other. Tweezer tips 13, 15 are carried at the distal ends of the arms and need not be covered by insulation. In the preferred embodiment, neither the outer surface nor the inner surface of tips 13, 15 is covered with insulation. Thus, the tweezer tips appear to the non-professional operator to be those with which the operator is familiar in conventional tweezers.

Figure 2:
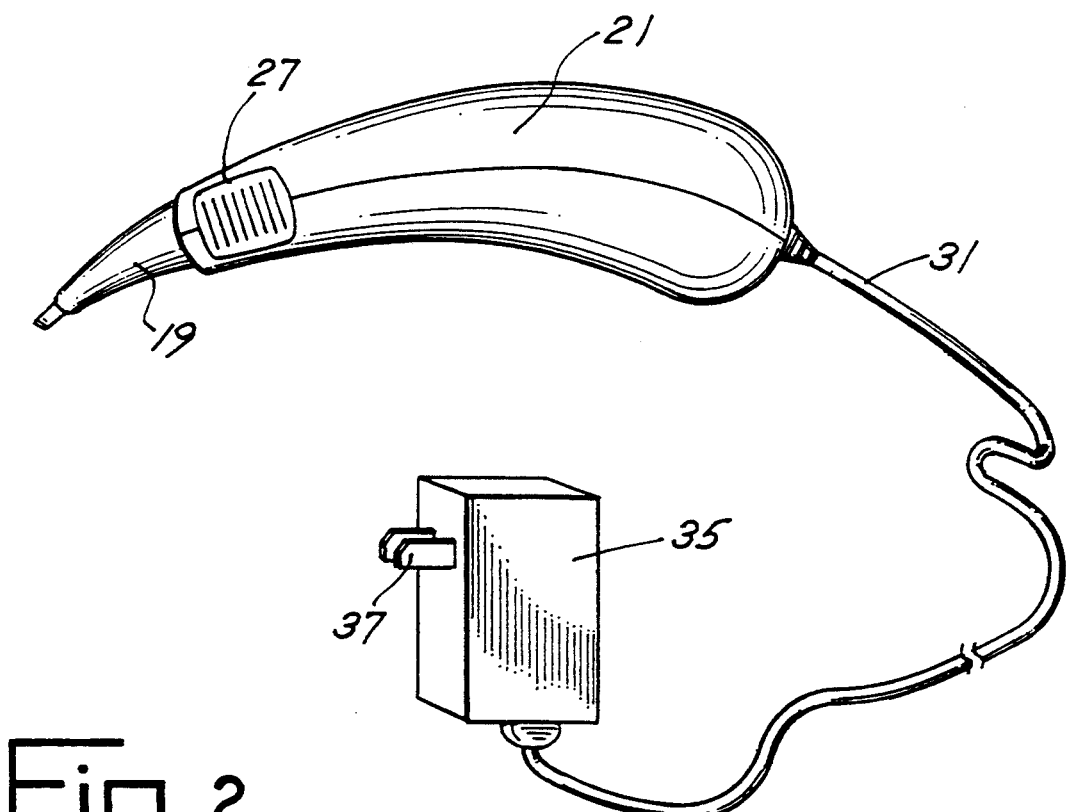
FIG. 2 is a side view of the electronic hair remover of FIG. 1.

As shown in FIG. 2, the longitudinal line or axis of casing 21 is curved. This provides a pleasing appearance to the casing as well as adapts the outer surface to a shape that is easily gripable by one hand of the operator. Tweezer arms 17, 19 are also shaped in a generally curved fashion, as shown in FIG. 2.

Referring again to FIG. 1, casing 21 houses a printed circuit board 23 which carries the printed circuit and circuit components of an electrical circuitry. The electrical circuitry generates and regulates the RF voltage signal which is applied to the hair via tweezer tips 13, 15.

As seen in FIG. 1, a pair of contact buttons 27, 29 are positioned on the sides of casing 21 just proximal of tweezer arms 17, 19. Pressing of the buttons toward one another mechanically closes together the two tips 13, 15 like a conventional pair of tweezers. Tweezer arms 17, 19 are spring mounted within casing 21 and a force applied to buttons 27, 29 moves the arms toward one another and against the spring bias. Releasing of the force from buttons 27, 29 serves to move the arms apart from each other due to the spring bias. In addition, in one embodiment, button switches 27, 29 are formed from touch sensitive contact switches which also serve to electrically control the circuit on printed circuit board 23, as described hereinafter.

As shown in FIG. 2, switches 27, 29 are shaped and positioned on the casing for receiving the operator's thumb and first index finger, permitting the operator to hold casing 21 with either a left hand or a right hand. The remaining fingers of the operator are positioned over the top of casing 21 to grip the casing into the palm of the operator's hand. The top of the casing is arched upwardly and the width of the casing is sized for fitting into the user's hand when the user positions a thumb and first index finger on buttons 27, 29.

As shown in FIG. 2, an electrical cord 31 serves as a power cord for supplying electrical voltage to a printed circuit board 23. Cord 31 is connected to an outlet transformer 35 which can be inserted into a conventional socket via plug elements 37. Transformer 35 converts conventional house current to a nominal 9 volt D.C. power supply which provides an output along cord 31. As understood, the voltage appearing on cord 31 need not be 9 volts, but may be higher or lower depending on the voltage needed by the circuitry.

In another embodiment, electronic hair remover 11 may be powered by a battery pack (not shown in FIGS. 1 and 2) which may be housed within casing 21 (or a tethered casing similar to 35). This provides a portable hair remover.

Figure 3:
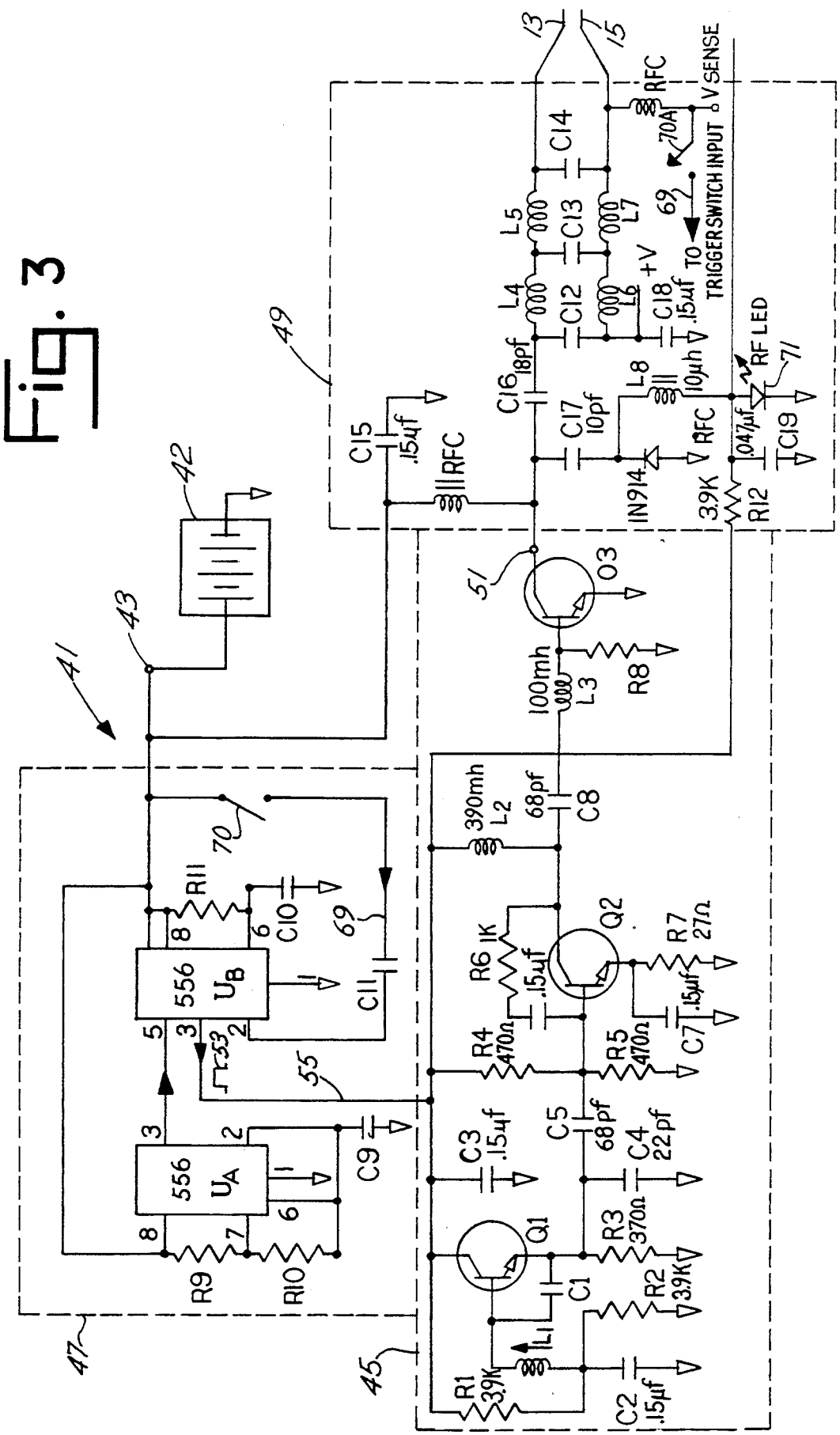
FIG. 3 is one embodiment of a circuitry for the electronic hair remover of FIG. 1.

Referring to FIG. 3, one embodiment of an electrical circuit 41 for use in casing 21 is shown. Circuit 41 serves to develop an RF oscillating voltage signal across tweezer tips 13, 15. The 9 volt power supply voltage appears at a circuit node 43 of circuit 41. Node 43 may be connected directly to electric cord 31 (FIG. 2) for receiving the 9 volt supply. In another embodiment, a battery pack 42 comprised of one or more batteries may be connected directly to node 43 so as to eliminate cord 31 and transformer box 35. The ground connection from cord 31, or from battery pack 42, is connected at various points in the circuit shown by an outlined arrowhead.

Circuit 41 includes an RF generator 45 which is controlled by a pulse timer 47. The output of generator 45 is delivered to and modified by an output interface 49 and then applied across tweezer tips 13, 15.

RF generator 45 is constructed from three transistors, Q1, Q2, and Q3 which are interconnected as shown. Generator 45 generates a voltage output signal at output node 51 having a nominal frequency of 27 megahertz ("MHz") and having an amplitude sufficient to treat a hair at its root area.

Transistor Q1 of generator 45 is configured as a Colpitts oscillator having its frequency of oscillation established by a capacitor C1 and an inductor L1. The capacitance to inductance ratio in the oscillator is kept high for yielding good frequency stability. Additionally, a crystal may be utilized in place of inductor L1 to improve the stability of the circuitry. Inductor L1 may be adjusted at the factory, for example, in order to establish the particular frequency setting of RF generator 45.

The oscillating output signal of the Colpitts oscillator appears at the emitter of transistor Q1 and passes to transistor Q2. Transistor Q2, together with transistor Q3, is connected in circuit for amplifying the amplitude of the oscillating voltage from transistor Q1. AC negative feedback used with transistor Q2, as well as impedance matching, controls the RF output voltage appearing across tips 13, 15.

The amplitude of the RF voltage is the major contributor to proper hair treatment and removal. Timer circuitry 41 controls the time of application of the high amplitude RF voltage. By controlling the time of application, or duty cycle, of the RF voltage, the average or real energy level which causes heat is minimized. Yet, a high peak RF voltage is produced to provide hair treatment. This reduction in power (but not voltage) removes the risk of creating electrical burns. Thus, power transistor Q3 is designed to maximize voltage gain.

Resistors R1–R8, capacitors C1–C8 and inductors L1–L3 are connected as shown for DC biasing and impedance matching, as understood.

Pulse timer 47 includes two integrated circuit components Ua and Ub, as well as resistors R9, R10, R11, and capacitors C9, C10, C11 interconnected as shown. Integrated circuit Ua is configured as a free running astable oscillator and is used to trigger integrated circuit Ub which is configured as a one shot multivibrator. Duty cycle and repetition rate is controlled via RC time constants. Pulse timer 47 controls the duration of the RF voltage pulse which appears across tweezer tips 13, 15. Pulse timer 47 establishes a very short pulse duration.

Pulse timer 47 develops a short duration voltage output pulse 53 along a conductor 55. The pulse is 9 volts in magnitude and is fed to RF generator 45. Pulse 53 serves to power up the RF generator during the time of the pulse duration. On the leading edge of pulse 53, RF generator 45 is turned ON. On the trailing edge of pulse 53, RF generator 45 is turned OFF.

A trigger input 69 serves to turn ON timer 47 whenever 9 volts appears on conductor 69. A simple switch 70 between the 9 volt supply 42 and trigger input 69 may be used to turn ON timer 47 whenever switch 70 is closed.

In one embodiment, buttons 27, 29 may be constructed from touch sensitive contact switches which close whenever touched by the operators fingers. Thus, the touching of contact switches on buttons 27, 29 serve to close switch 70 (the touch sensitive contact switch) and turn ON pulse timer 47.

In another embodiment, switch 70 is formed of a small contact plunger switch (not shown) located at the base of the tweezer arms 17, 19. The plunger switch engages the skin when the tweezer arms 17, 19 are brought near to the body and closes switch 70 in accordance with the distance that the tweezer arms are spaced from the skin. For example, a voltage level V sense may be applied through such a plunger switch (represented at 70A) via coil RFC.

The closing of switch 70 develops current along conductor 69 and serves to provide a trigger input signal to timer circuit 47. The input signal on conductor 69 turns on pulse timer 47 so that pulses 53 will be successively generated to RF generator 45.

As understood from above, switch 70 forms the ON/OFF switch of the hair remover 11. Switch 70 may be a separate ON/OFF switch located on the casing for actuation by the operator to power up the system, or may be located on the finger actuation buttons 27, 29, for powering up the system when the operator has his fingers on buttons 27, 29, or may be a switch which is responsive to the distance that the tweezer tips are spaced from the skin.

As shown in FIG. 3, output interface 49 receives the short duration voltage RF pulse appearing at output node 51 from generator 45. Interface 49 varies the amplitude of the RF pulses as a function of the distance that tweezer tips 13, 15 are located from the user's skin.

Interface 49 is constructed to simulate an artificial transmission line. Capacitors C12, C13, C14 and inductors L4, L5 are chosen to simulate a resident coaxial line. The selection of values for capacitors C12–C14 and inductors L4–L5 is made in accordance with the capacitive load across tweezer tips 13, 15. In this manner, the artificial transmission line will operate as a tuned circuit and with as high a resonance Q value as possible. The voltage at the end of the artificial transmission line which then appears across tweezer tips 13, 15 will be multiplied by a factor of Q times the input voltage to the artificial transmission line. Typically, this is two to four times the input voltage to the artificial transmission line, and is limited by the losses in the artificial line.

The RF voltage amplitude at the tweezer tips 13, 15 is reduced when the tweezer tips are in contact with the user's skin with the proper choice of capacitors C12–C14 and inductors L4–L5. Capacitor C14 is selected to be smaller than that required to achieve maximum RF voltage amplitude. The additional required output capacitance needed to provide maximum RF voltage is provided by the capacitance between the user's skin and the tweezer tips 13, 15. Thus, interface unit 49 serves to adjust the amplitude of the output RF voltage in accordance with the distance that tweezer tips 13, 15 are from the skin, because the skin's capacitance is "connected" in parallel with capacitor C14. That is, with a hair between the tips 13, 15 and the tips above the skin a certain capacitance is connected in parallel with capacitor C14. However, with the tips touching the skin, another different capacitance is connected in parallel with capacitor C14.

As an alternate embodiment, output interface 49 may be removed from the circuit and the voltage appearing at output node 51, or an amplification thereof, may be impressed directly across tweezer tips 13, 15. In addition, if desired, a mechanical switch may be used to monitor the distance of the tweezer tips from the skin to provide a trigger output on conductor 69.

As another alternate embodiment, instead of monitoring the capacitance of the skin between tweezer tips 13, 15, the circuitry for monitoring capacitance in interface 49 may be replaced by circuitry for monitoring the resistance or conductivity of the skin. In response to monitoring such a characteristic related to contact or closeness of the tweezer tips to the skin (hereinafter a characteristic of skin proximity), the amplitude of the RF voltage signal appearing across tips 13, 15 is adjusted.

In order to indicate the presence of RF energy at the tweezer tips, an LED 71 is used. LED 71 turns ON to provide a visual indication that RF energy is being conducted to the tweezer tips 13, 15.

Figure 4:
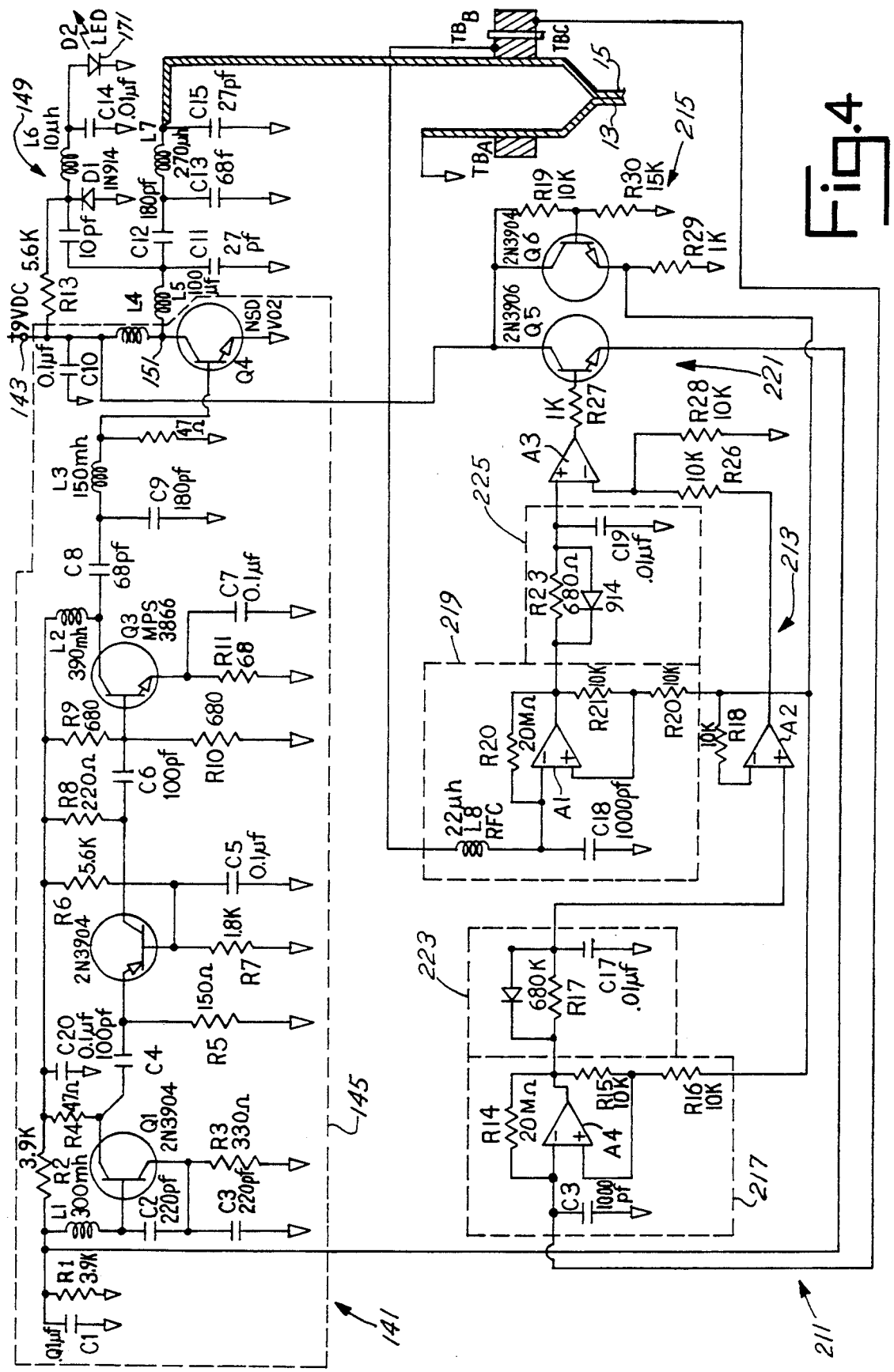
FIG. 4 is another embodiment of a circuitry for the electronic hair remover of FIG. 1.

Referring to FIG. 4, a second embodiment of an electrical circuit 141 for use in casing 21 is shown. Circuit 141 develops an RF oscillating voltage signal across tweezer tips 13, 15. A nine volt power supply voltage appears at a circuit node 143 of the circuit 141. Circuit 141 includes an RF generator 145, similar to RF generator 45 of FIG. 3. The output of generator 145 is delivered to and modified by an output interface 149 and then applied across tweezer tips 13, 15.

The output of generator 145 is controlled by a touch sensitive ON/OFF circuit 211 and a skin detect circuit 213. Touch sensitive ON/OFF circuit 211 and skin detect circuit 213 are each constructed from a pair of operational amplifiers A1–A4. Operational amplifiers A1, A3 form a skin detect circuit 213. Operation amplifiers A4, A2 form the touch sensitive ON/OFF circuit 211.

A voltage reference supply circuit 215 comprises a transistor Q6 and resistors R19, R29, R30. Supply circuit 215 provides a reference voltage supply for biasing operational amplifiers A1, A2, A4 at half voltage supply.

An electronic switch 221 includes a transistor Q5 which is controlled by operational amplifier A3. Amplifier A3 is constructed as a voltage comparator. Switch 221 establishes the ON/OFF condition of the RF power oscillator 145. Transistor Q4 of power oscillator 145 operates as a class C voltage amplifier, and therefore no major power drain will occur until the RF oscillator 145 is turned ON via transistor Q5.

Operational amplifiers A1, A4 each form separate resistance sample circuits 217, 219. Op amps A1, A4 operate as an RC oscillator whose charge and discharge rate is controlled by capacitor C18, resistor R20 and capacitor C16, resistor R14, respectively.

The noninverting input of amplifier A1 is biased at half power supply and operates as a voltage comparator input. The other comparator input of amplifier A1 is supplied via the charge and discharge voltage supplied via capacitor C18. Assuming the output of operational amplifier A1 is high, the inverting input of operational amplifier A1 will rise at the rate of RC (resistor R20, capacitor C18). When the inverting input is at half voltage supply (equal to the noninverting input), the output of amplifier A1 goes low. Consequently, the voltage across the capacitor C18 will fall at a rate RC until the noninverting input of op amp A1 falls below half the voltage supply and the cycle repeats itself. As long as the discharge rate is not less than the charge rate, the cycle will repeat itself. Operational amplifier A4 works in a similar manner in resistance sample circuit 217.

The occurrence of body resistance, typically 20 Meg. Ohms or less, is sampled by operational amplifiers A1 and A4. Operational amplifier A4 samples the resistance between touch contact TBA and touch contact TBC positioned on buttons 27, 29 respectively. Operational amplifier A1 samples the resistance between tweezer tip 15 (at contact TBB) and tweezer tip 13 (at contact TBA). Contacts TBB and TBC are insulated from one another.

Thus, resistance sample circuits 217, 219 serve to sample particular resistance levels. The output of each resistance sample circuit 217, 219 will either be a square wave RC oscillator signal (for resistance samples greater than 20 meg ohm) or a positive voltage of the voltage supply (9 volts for example) for resistance samples less then 20 meg ohms.

Each of the outputs of resistance sample circuits 217, 219 are applied to a respective voltage integrator 223, 225. Integrator 223 is comprised of a resistor R17, diode D3, and capacitor C17. Integrator 225 is comprised of resistor R23, diode D4, and capacitor C19. Each of integrators 223, 225 provides a slow charge time and a rapid discharge time. If the output of the resistance sample circuits 217, 219 is a square wave voltage signal, the output of the integrators 223, 225 is a slow rising wave with a fast fall time. The average value of this voltage is low. When the resistant sample is below 20 meg ohms, the voltage is high. This low or high voltage output from integrators 223, 225 are used to control voltage comparator A3 which in turn controls the RF power oscillator 145 via transistor switch Q5.

The RF power oscillator 145 will only operate when the touch sensitive ON/OFF circuit 211 is active, indicating that the operator is touching contacts TBA, TBC. When the operator places his fingers on both contacts TBA and TBC, resistance sample circuit 217 turns OFF and its output goes HIGH. This causes the output of op amp A2 to go HIGH.

When the input to the inverting input of comparator A3 is forced HIGH, transistor Q5 is forced ON to enable the RF power oscillator 145. If the operator removes his finger tips from tweezer contacts TBA, TBC, operational amplifier A4 will oscillate forcing the noninverting input of op amp A2 low. This will cause op amp A3 to go LOW turning OFF transistor Q5 and thus inhibiting the RF power oscillator 145.

When op amp A4 is turned OFF and not oscillating, the comparator A3 is enabled to monitor the sample resistant circuit 219. The role of circuit 219 is the converse of the ON/OFF touch control circuit 211. As long as no contact to the body or skin is made, by the tweezer tips, the noninverting input to comparator A3 is low. Thus, transistor switch Q5 is enabled and so is the RF power oscillator 145.

Resistant sample circuit 219 monitors the resistance between tweezer contacts TBA and TBB. This resistance is continuously monitored for determining whether skin contact occurs. If skin contact does occur, the unit is immediately shut down. The resistance is monitored along conductor 251 which provides an input to the noninverting input of op amp A1.

Proper selection of time constance of resistors R20, R23 and capacitors C18, C19 will provide a detection circuit that will pulse the transistor switch Q5. This is required for an RF power oscillator with an increased output RF voltage. The duty cycle of this pulse is selected by altering the ratios of resistors R26, R28.

Similar to LED 71, an LED 171 is used to indicate that RF energy is being conducted to the tweezer tips 13, 15.

The above describes several circuitry embodiments for delivering RF energy and monitoring the position, location, and skin contact of the tweezer assembly for safety. However, it should be noted that there are other circuits which could be used in accordance with what is taught herein.

Because the time duration of the voltage pulse across tweezer tips 13, 15 is relatively short, the amount of power consumed is minimized. Pulse switching of the RF generator allows a higher peak RF voltage to be generated, but of extremely short duration. Thus, any possible heating effects which might burn the skin are eliminated. The pulse is nevertheless sufficiently intense in amplitude to destroy the root hair and discourage subsequent root growth.

Operation of the electronic hair remover is easy and straight forward. The electronic hair remover is held in one hand of the user. The user places open tweezer tips 13, 15 proximate the hair to be removed. Switch buttons 27, 29 actuated to cause the tweezer tips to grip the hair. Actuation by merely touching, for example, of switch buttons 27, 29 also serves to turn on the circuit. Instead of RF energy being delivered to tweezer tips 13, 15 on a constant basis, the electronic hair remover via interface 49 constantly monitors a characteristic of skin proximity before switching RF pulsed energy to tweezer tips 13, 15 to treat the hair root and remove the hair. The electrical circuit of interface 49 "checks" the capacitance between opposing tweezer tips 13, 15 for the existence of a hair or skin and adjusts the RF voltage amplitude accordingly. In addition, a mechanical switch or resistance contact sense circuit may be used, if desired, which senses actual contact between skin and tweezer tips 13, 15 before emitting pulse RF waves.

It is to be understood, of course, that the foregoing describes preferred embodiments of the present invention, and that modifications may be made therein without departing from the spirit or scope of the present invention as set forth in the appended claims.

What is claimed is:

1. An electronic hair remover using high radio frequency (RF) energy to treat hair comprising:

(a) a hand-holdable casing having a top side, a bottom side and two opposite sides, said casing having:
  (i) a tweezer presenting end being of a narrow configuration; and
  (ii) a hand holding end opposite said tweezer presenting end, said hand holding end being of a wide configuration for nesting in a user's hand and having a top surface on said top side being arched upwardly;
(b) an activatable tweezer assembly projecting from said tweezer presenting end of said casing and having two opposing electrically conductive tweezer tips;
(c) a pair of buttons positioned on said opposite sides of said casing for activation of said tweezer assembly, said buttons being shaped for receiving the thumb and first index finger of the user's hand, permitting the remaining fingers of the user's hand to be positioned over said top surface of said casing to grip said casing into the palm of the user's hand; and
(d) an RF generator for generating RF energy in the form of an electrical signal of high amplitude voltage, said generator contained within said casing and electrically connected in circuit with said tweezer tips.

2. The electronic hair remover of claim 1 wherein said top side of said casing is generally pear shaped such that said hand holding end is wider than said tweezer presenting end.

3. The electronic hair remover of claim 2 wherein said pair of buttons are located proximate to said tweezer presenting end of said casing.

4. The electronic hair remover of claim 1 further comprising a bottom surface on said bottom side, said bottom surface being arched generally upwardly in generally the same fashion as said top surface to accommodate said remaining fingers of the user's hand.

5. The electronic hair remover of claim 1 wherein said RF generator includes a battery.

6. The electronic hair remover of claim 5 wherein said hair remover is of a size such that it is portable.

7. The electronic hair remover of claim 1 wherein said RF generator includes source of electric current.

8. The electronic hair remover of claim 1 wherein said tweezer tips are constructed of an electrically conducting material.

9. The electronic hair remover of claim 1 wherein said pair of buttons are generally rectangular in shape.

10. The electronic hair remover of claim 1 wherein the center of each button of said pair of buttons is slightly depressed relative to its periphery for ease of activation.

11. The electronic hair remover of claim 1 wherein said tweezer assembly projecting from said tweezer presenting end of said casing is curved and sloped generally downward.

12. The electronic hair remover of claim 1 wherein said tweezer assembly comprises a pair of tweezer arms projecting outwardly from said tweezer presenting end of said casing said tweezer arms being integral with said tweezer tips.

13. The electronic hair remover of claim 12 wherein said tweezer arms are generally parallel to each other.

14. The electronic hair remover of claim 12 wherein said tweezer arms projecting from said tweezer presenting end generally converge.

* * * * *